United States Patent [19]

Bhattacharya

[11] Patent Number: 5,338,859
[45] Date of Patent: Aug. 16, 1994

[54] PROCESS FOR THE PRODUCTION OF CALCIUM SALTS OF HYDANTOIC ACIDS

[75] Inventor: Apurba Bhattacharya, Corpus Christi, Tex.

[73] Assignee: Hoechst Celanese Corporation, Sommerville, N.J.

[21] Appl. No.: 16,628

[22] Filed: Feb. 12, 1993

[51] Int. Cl.$^5$ .............. C07D 233/90; C07D 211/60; C07D 207/16; C07C 149/247

[52] U.S. Cl. .............. 548/312.1; 548/314.4; 548/317.1; 548/492; 548/532; 562/443; 562/446; 562/539; 562/560; 562/561; 546/227

[58] Field of Search .............. 562/539, 560, 561, 443, 562/446; 548/312.1, 317.1, 314.4

[56] References Cited

U.S. PATENT DOCUMENTS

| | | | |
|---|---|---|---|
| 2,557,920 | 6/1951 | White | 562/559 X |
| 3,668,221 | 6/1972 | Shima et al. | 562/559 X |
| 3,790,599 | 2/1974 | Zundel | 562/559 X |
| 3,833,651 | 9/1974 | Ouchi et al. | 562/559 |
| 3,917,683 | 11/1975 | Ouchi et al. | 562/559 |
| 4,069,251 | 1/1978 | Mannsfeld et al. | 562/559 |
| 4,272,631 | 6/1981 | Schaaf et al. | 562/559 |
| 4,391,988 | 7/1983 | Spindler et al. | 562/559 |
| 4,436,910 | 3/1984 | Kleemann et al. | 546/245 |
| 4,518,801 | 5/1985 | Bolze et al. | 562/559 |

*Primary Examiner*—Floyd D. Higel
*Attorney, Agent, or Firm*—James J. Mullen; Donald R. Cassady

[57] ABSTRACT

The present invention provides a process for the production of calcium salts of hydantoic acids and which comprises the steps of reacting a hydantoin with a calcium base material such as calcium hydroxide in an aqueous medium at a sufficient temperature and for a sufficient period of time to form the calcium salt of the corresponding hydantoic acid and then separating the calcium salt of such acid from the reaction mass. This separation can include the further steps of cooling the reaction mass down to facilitate the precipitation of the acid/salt crystals and then separating the precipitate by means of filtering or centrifugating. These acids can then be subjected to a $HNO_2$-mediated decarbamoylation process followed by an optical resolution step to thus provide high yields of D-p-hydroxyphenylglycine which is a key synthetic immediate or building block for semi-synthetic penicillin and cephalosporins.

14 Claims, No Drawings

PROCESS FOR THE PRODUCTION OF CALCIUM SALTS OF HYDANTOIC ACIDS

BACKGROUND OF THE INVENTION

The present invention is directed to a process for the production of calcium salts of hydantoic acids and specifically relates to the preparation of such acids from the corresponding hydantoin by treatment of the latter with a calcium base material.

D-p-hydroxyphenylglycine (DpHPG) is a key synthetic intermediate or building block for semi-synthetic penicillin and cephalosporins. There are various routes to prepare DpHPG and those include using hydantoins as an intermediate to the final DpHPG material. Such processes and other genetic processes for preparing glycines from hydantoins are generally disclosed in U.S. Pat. Nos. 5,147,664; 5,120,855; 4,960,932; 4,716,246; 4,621,153; 4,518,801; 4,436,910; 4,069,251; co-pending U.S. patent application Ser. No. 07/649,782 filed Jan. 31, 1991, entitled, "Precipitation-Induced Asymmetric Transformation of Chiral Alpha-Amino Acids and Salts Thereof", and which is assigned to the same Assignee as the present application; and Japanese patent application 55/104890 filed Aug. 11, 1980, and all of which are incorporated herein by reference in their entirety.

Some of the major problems with the processes disclosed in the prior art as exemplified by the above-identified patents and patent applications are the low yields of the desired end product and the formation of troublesome and unwanted by-products.

The disadvantages of the prior art are overcome by the present invention wherein there is provided a process for preparing hydantoic acids from their corresponding hydantoins by a very efficient and low cost method. The resultant hydantoic acids can then be subjected to a $HNO_2$-mediated decarbamoylation process followed by an optical resolution step to thus provide high yields of DpHPG.

SUMMARY OF THE INVENTION

The present invention provides a process which comprises the steps of reacting a hydantoin with a calcium base material in an aqueous medium at a sufficient temperature and for a sufficient period of time to form the calcium salt of the corresponding hydantoic acid and then separating the calcium salt of such acid from the reaction mass. This reaction can include the further steps of cooling the reaction mass down to facilitate the precipitation of the acid/salt crystals and then separating the precipitate by means of filtering or centrifugating.

DESCRIPTION OF THE INVENTION

The process of the present invention comprises the steps of (1) reacting a hydantoin having the formula:

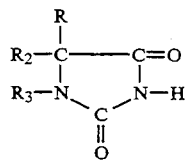

wherein $R_1$, $R_2$, and $R_3$ (defined below) with a calcium base material such as calcium hydroxide at a sufficient temperature and for a sufficient period of time to form the calcium salt of the corresponding hydantoic acid, and (2) separating the calcium salt of such acid from the reaction mass. It was unexpectedly found that this process results in substantially high yields and substantially no by-products.

In the process of the invention there can be employed any hydantoin, for example, those of the formula:

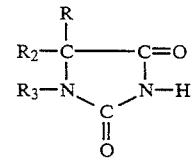

where $R_1$ and $R_2$ are the same or different and are a hydrogen straight or branched chain one (1) to twenty (20) carbon atom alkyl group, e.g., methyl, ethyl, propyl, isobutyl, t-butyl, amyl, hexyl, octyl, decyl, hexadecyl, eicosamyl, which alkyl group can be substituted, or a straight or branched chain alkenyl group with two (2) to ten (10) carbon atoms, e.g. vinyl, allyl, methallyl, crotyl, 9-decenyl, a straight or branched chain alkinyl group with two (2) to six (6) carbon atoms, e.g. ethinyl, propinyl, 2-hexinyl, a cycloalkyl group or cycloalkenyl group with three (3) to eight (8) carbon atoms, e.g. cyclopropyl, cyclopentyl, cyclohexyl, cyclooctyl, cyclopentenyl, cyclohexenyl, cyclooctenyl, or a phenyl group which in a given case can be substituted, e.g., where the substituent is hydroxy, halogen, alkoxy or phenoxy, $R_3$ is hydrogen or an alkyl group with one (1) to ten (10) carbon atoms, e.g., methyl, ethyl, propyl, butyl, isobutyl, amyl, hexyl, octyl or decyl or $R_1$ and $R_2$ or $R_2$ and $R_3$ together are an alkylene group having three (3) to five (5) carbon atoms, e.g., trimethylene, tetramethylene, or pentwnethylene. If $R_1$ and/or $R_2$ is a substituted alkyl group having one (1) to twenty (20) carbon atoms as substituents there can be used for example phenyl, halophenyl, e.g. 4-fluorophenyl, 4-chlorophenyl, hydroxyphenyl, e.g., 4-hydroxyphenyl, 3-hydroxyphenyl, 3,4-dihydroxyphenyl, alkoxyphenyl, e.g. 3-methoxyphenyl, 4-ethoxyphenyl, 3,4-dimethoxyphenyl, 3-indolyl, sulfur functions, e.g. 4-hydantoyl, 2′,3′-dithiobutyl, carboxy groups, e.g. carboxymethyl, carboxyethyl, carboxypropyl, carboxybutyl, carboxamide groups, e.g. carboxamidomethyl, carboxamidoethyl, halogen, e.g. fluorine, chlorine, bromine, and iodine (especially fluorine and chlorine), e.g. fluoromethyl, chloromethyl, bromomethyl, fluoroethyl, chloroethyl, fluorobutyl, chlorobutyl, fluorodecyl, fluoroeicosamyl, chloroeicosamyl, cycloalkyl group with three (3) to eight (8) carbon atoms, e.g. cyclopropylmethyl, cyclohexylmethyl, cyclohexylethyl, or cycloalkenyl groups having three (3) to eight (8) carbon atoms, e.g. cyclopentenylethyl or cyclohexylmethyl. If $R_1$ and/or $R_2$ is a substituted phenyl it can be for example a hydroxyphenyl group, e.g. 4-hydroxyphenyl, 3,4-dihydroxyphenyl or 3-hydroxyphenyl, a halophenyl group, e.g. 4-chlorophenyl, 4-fluorophenyl, 4-bromophenyl, 2,4-dichlorophenyl, 2,4-difluorophenyl, a phenoxyphenyl group, e.g. 3-phenoxyphenyl, or alkoxyphenyl, e.g. 4-methoxyphenyl, 3,4-dimethoxyphenyl.

Examples of such hydantoins are the base material hydantoin, 5-methylhydantoin, 5-n-propylhydantoin, 5-i-propylhydantoin, 5-i-butylhydantoin, 5-sec.-butylhydantoin, 5-n-pentadecylhydantoin, 5-phenylhydantoin, 5-(4′-hydroxyphenyl)-hydantoin, 5-(4′-fluorophenyl)-hydantoin, 5(3′-phenoxyphenyl)hydantoin, 5- benzyl-hydantoin, 5-(3'-4'-dihydroxybenzyl)-hydantoin, 5-[indolyl-(3)-methyl]-hydantoin, 5-4'-hydanto-5-yl-2',3'-dithia-butyl]-hydantoin, 5-carboxymethylhydantoin, 5-amidomethylhydantoin, 5-(2'-carboxyethyl)-hydantoin, 5-2'-amidoethyl)-hydantoin, 5-fluormethyl-hydantoin, 5-chloromethylhydantoin, 5-cyclohexyl-hydantoin, 5-cyclopentylhydantoin, 5-(cyclohexylmethyl)-hydantoin, 5-[cyclohex-3-en-1-yl]-hydantoin, 5-[cyclohex-3-en-1-yl-methyl]hydantoin, 5-vinylhydantoin, 5-ethinylhydantoin, 5-(4'-methoxyphenylmethyl)-hydantoin, 5-(3',4'-dimethoxyphenylmethyl)-hydantoin, 5-4'-hydroxybenzyl)-5-vinyl-hydantoin, 5-benzyl-5-ethinyl-hydantoin, 5,5-dimethyl-hydantoin, 5,5-tetramethylenhydantoin, 5,5-trimethylenhydantoin, 1,5-trimethylenhydantoin, or 1,5-tetramethylhydantoin.

Additional substituted hydantoins include 5-n-eicosamylhydantoin, 5,5-diethylhydantoin, 5-methyl-5-ethylhydantoin, 5-allylhydantoin, 5-methallylhydantoin, 5-decen-9-ylhydantoin, 5-hexinylhydantoin, 5-cyclooctylhydantoin, 5-cyclopropylhydantoin, 1-methylhydantoin, 1,5-dimethylhydantoin, 1,5,5-trimethylhydantoin, 1-ethylhydantoin, 1-butylhydantoin, 5,5-pentamethylenehydantoin, 5-fluoroethylhydantoin, 5-chloroethylhydantoin, 5-(4'-chlorophenyl)hydantoin, 5,5-diphenylhydantoin, 5-methyl-5-phenylhydantoin, or 5-3',4'-dimethoxyphenyl)hydantoin.

The process of this invention is generally carried out at a temperature sufficient to convert the hydantoin to its corresponding calcium salt of the hydantoic acid. Such temperature is from about 50° C. to about 180° C. and preferably from about 75° C. to about 150° C. Once the calcium salt of the hydantoic acid is formed, it may be necessary to cool the resultant reaction mass to a temperature below 50° C. in order to separate the acid/salt crystals from the reaction mass. This cooling can take place at any temperature below 50° C. in order to effectuate the desired end result. Such cooling can be conducted at from about 0° C. to about 50° C., and preferably from about 5° C. to about 40° C.

One of the unique features of the present invention is the use of a calcium base material to convert the hydantoin to the corresponding hydantoic acid. This calcium base material is any calcium containing material which can break the immediate "hydantoin ring" and facilitate the production and subsequent precipitation of the hydantoic acid salt from the aqueous solution/reaction mass. Such materials include calcium hydroxide, calcium oxide, calcium acetate, calcium thiocyanate [Ca(SCN)$_2$], calcium phosphate [Ca$_3$(PO$_4$)$_2$] and the like.

The facile precipitation of the calcium salt of the hydantoic acid from the aqueous solution is the driving force which shifts the equilibrium to the right and thus promotes substantially high yields of the desired end product. While this is the apparent rationale of some of the chemistry behind the inventive concept, Applicant does not wish to be limited by any theoretical discussion of the same. While the present invention is directed to the use of a calcium base material, it is also within the scope of the inventive concept that other members of Group IIA of the Periodic Chart of Elements could be used. It is to be understood that the term "Group IIA base material", as used herein, covers and includes all members of Group IIA of the Periodic Chart of Elements such as Ca, Mg, Sr, and Ba, and which members can be in the hydroxide, oxide, acetate, thiocyanate, and phosphate forms thereof. However, the description herein will be generally directed to the use of a calcium base material such as calcium hydroxide.

The amount of calcium base material, e.g. calcium oxide or hydroxide, is exactly what is required for the hydrolysis of the hydantoin ring. If the hydantoin to be hydrolyzed contains more than one (1) hydantoin ring, e.g. in the case of the dihydantoin of cystine, naturally there must be employed the multiple amount. If the hydantoin to be hydrolyzed contains a carboxyl or carboxamide group, then there must be employed a further equivalent of calcium base material. Finally, if there is employed a crude aqueous solution of a hydantoin which still contains excess of ammonium carbonate from a hydantoin synthesis, then it is necessary either to drive off this ammonium carbonate before the reaction by a treatment with steam or, which is simpler, to add an additional amount of calcium oxide or hydroxide equivalent to the content of carbonate ions.

The pressure employed in the practice of the present invention is that which will be sufficient to carry out the reaction to achieve the desired end product. The pressure can be atmospheric, subatmospheric, or superamospheric.

The hydantoin can be employed in the process of the invention in the racemic D,L-form or in the form of D- or L-enantiomer.

The process of the invention is explained in more detail in the following examples. All percentages given are percent by weight.

The process can comprise, consist essentially of, or consist of the stated steps with the recited materials.

EXAMPLE 1

A 500 ml, 3-necked, round-bottom flask equipped with a mechanical stirrer, nitrogen inlet, thermowell, and a reflux condenser was charged with p-hydroxyphenylhydantoin (19.2 g, 100 mmol), calcium hydroxide (7.4 g, 100 mmol) and water (120 ml). The flask was evacuated and flushed with nitrogen three (3) times. The stirred suspension was heated to reflux with a heating mantle (batch temperature 100° C.) under nitrogen atmosphere. After refluxing for four (4) hours, complete disappearance of starting material was observed by high pressure liquid chromatography (HPLC). The reflux condenser was then replaced with a distillation head and the stirred suspension was distilled with simultaneous addition of isopropanol at such a rate that the total volume was maintained at approximately 120 ml. After addition of approximately 150 ml isopropanol, the distillation head showed a temperature of 82° C. Distillation was discontinued at this point. The suspension was cooled to 22° C. and stirred for an additional two (2) hours. The crystals were filtered, washed with 40 ml isopropanol, and dried at 40° C. under house vacuum overnight, affording 20.6 g (90% yield) of p-hydroxyphenylhydantoic acid.

EXAMPLES 2–16

The procedure set forth in Example 1 is used with the exception of the below-listed hydantoin derivatives are employed instead of hydantoin per se. The results are set forth in the following table:

| EXAMPLE | HYDANTOIN DERIVATIVES EMPLOYED | OBTAINED: CALCIUM SALT OF: | YIELD (IN % OF THEORY) |
|---|---|---|---|
| 2 | 5-phenylhydantoin | 2-phenylhydantoic acid | 86 |
| 3 | 5-i-butylhydantoin | 2-isobutylhydantoic acid | 90 |
| 4 | 5-(4'-hydroxyphenyl)-hydantoin | 2(4'-hydroxyphenyl-hydantoic acid | 91 |
| 5 | 5-(indolyl-3-methyl)-hydantoin | 2-(indoyl-3-methyl) hydantoic acid | 89 |
| 6 | 5-fluormethyl-hydantoin | 2-fluoromethyl hydantoic acid | 85 |
| 7 | 5-cyclohexyl-hydantoin | 2-cyclohexyl hydantoic acid | 93 |
| 8 | 5-cyclohexylmethyl)-hydantoin | 2-cyclohexylmethyl) hydantoic acid | 90 |
| 9 | 5-(4'-hydroxybenzyl)-hydantoin | 2(4'-hydroxybenzyl) hydantoic acid | 92 |
| 10 | 5-(3',4'-dihydroxy-benzyl)-hydantoin | 2(3',4'-dihhydroxybenzyl) hydantoic acid | 88 |
| 11 | 5-(4'-methoxybenzyl)-hydantoin | 2-(4'-methoxybenzyl) hydantoic acid | 84 |
| 12 | 5-vinylhydantoin | 2-vinyl hydantoic acid | 87 |
| 13 | 5-benzyl-5-ethinyl-hydantoin | 2-benzyl-2-ethinyl hydantoic acid | 91 |
| 14 | 5,5-trimethylene-hydantoin | 2,2-trimethylene hydantoic acid | 94 |
| 15 | 1,5-trimethylene-hydantoin | 2,3-trimethylene hydantoic acid | 91 |
| 16 | 1,5-tetramethylene-hydantoin | 2,3-tetramethylene hydantoic acid | 93 |

EXAMPLE 17 (COMPARATIVE)

Example 1 of U.S. Pat. No. 4,436,910 was generally repeated as follows: p-hydroxyphenyl hydantoin (100 mM, 19.2 g) was treated with NaOH (100 mM, 4.0 g) and Ca(OH)$_2$ (200 mM, 14.2 g) in 200 ml water at 140° C. for four hours in an autoclave. After cooling to 50° C., the precipitated CaCO$_3$ which separated out was filtered off. The recovered mother liquor was analyzed by HPLC. It was found to contain 1.16 g p-hydroxyphenyl glycine (7% yield) in solution. Substantial amounts of decomposition (by-product) was indicated by HPLC analysis. This control experiment demonstrates that the p-hydroxyphenylglycine product when subjected under the reaction conditions [Ca(OH)$_2$, NaOH, 140° C., H$_2$O] suffers severe decomposition to several unwanted and unidentified products. It was quite unexpected then to find that the use per se of only a calcium base material like calcium hydroxide facilitates the production of the corresponding hydantoic acid salt in very high yields. The hydantoic acid salt can then be subjected to decarbamoylation with nitrous acid under acidic conditions to produce p-hydroxyphenylglycine, and which can in turn be optically resolved by processes such as described in U.S. Pat. Nos. 5,120,855 and 3,094,741, both of which are incorporated herein by reference in their entirety.

EXAMPLE 18

Example 1 above was repeated except that magnesium hydroxide was substituted for calcium hydroxide. The yield of the final magnesium salt of the hydantoic acid was 87%.

It is understood that the above examples are given by way of illustration and that many variations can be made without departing from the spirit and scope of the present invention as encompassed by the following claims.

What is claimed is:

1. A process for the production of a calcium salt of a hydantoic acid comprising reacting a hydantoin at a temperature between 50° C. and 180° C. with a calcium base and separating the precipitated calcium salt of the hydantoic acid.

2. A process according to claim 1 wherein the reaction of the hydantoin is carried out at 75° C. to 150° C.

3. A process according to claim 1 wherein the hydantoin employed has the formula:

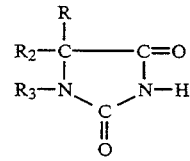

where R$_1$ and R$_2$ are (1) hydrogen, (2) one to twenty carbon atom alkyl, (3) substituted one to twenty carbon atom alkyl wherein the substituent is phenyl, hydroxyphenyl, alkoxyphenyl, halophenyl, indolyl, sulfur, carboxy, carboxamido, halogen, cycloalkyl of three to eight carbon atoms or cycloalkenyl of three to eight carbon atoms, (4) two to ten carbon atom alkenyl, (5) two to six carbon atom alkinyl, (6) three to eight carbon atom cycloalkyl, (7) three to eight carbon atom cycloalkenyl, (8) phenyl or (9) substituted phenyl wherein the substituent is hydroxy, halogen, alkoxy, phenoxy, or R$_1$ and R$_2$ together or R$_2$ and R$_3$ together are an alkylene group having three to five carbon atoms and R$_3$ is hydrogen or a one to ten carbon atom alkyl.

4. A process according to claim 3 wherein when one of R$_1$ and R$_2$ is 4-hydanto-5-yl-2,3-dithiabutyl and the other of R$_1$ and R$_2$ is hydrogen.

5. A process according to claim 4 wherein R$_2$ is hydrogen.

6. A process according to claim 4 wherein R$_1$ and R$_2$ together are three to five carbon atom alkylene and R$_3$ is hydrogen or R$_2$ and R$_3$ together are three to five carbon atom alkylene and R$_1$ is hydrogen.

7. A process according to claim 4 wherein the starting hydantoin compound is hydantoin per se, 5,5-dimethylhydantoin, 5-benzylhydantoin, 5-methylhydantoin, 5-phenylhydantoin, 5-isobutylhydantoin, 5-(4'-hydroxyphenyl)-hydantoin, 5-(indolyl-3-methyl)-hydantoin, 5-fluoromethylhydantoin, 5-cyclohexyl-hydantoin, 5-(cyclohexylmethyl)hydantoin, 5-(3', 4'-dihydroxybenzyl)-hydantoin, 5-(4'-methoxybenzyl-hydantoin, 5-vinylhydantoin, 5-benzyl-5-ethinylhydantoin, 5,5-trimethylenehydantoin, 1,5-trimethylenehydantoin, 5,5-tetramethylenehydantoin, 5-carboxymethylhydantoin, 5-(carboxamidomethyl)-hydantoin, 5-2'-carboxyethyl)-hydantoin, 5-(2'-carboxamidoethyl)-hydantoin, or 5-(4'-hydanto-5-yl-2',3'-dithia-butyl)-hydantoin and the α-aminocarboxylic acid salt formed is the calcium salt of glycine, α-aminoisobutyric acid, phenylalanine, alanine, phenylglycine, leucine, 4-hydroxyphenylglycine, tryptophan, 3-fluoroalanine, 2-cyclohexylglycine, 3-cyclohexylalanine, tyrosine, 3,4-dihydroxyphenylalanine, 4-methoxyphenylalanine, 2-amino-vinyl-acetic acid, α-ethinyl-phenylalanine, 1-aminocyclopentane carboxylic acid, proline, pipecolic acid, aspartic acid, glutamic acid or cystine.

8. A process according to claim 1 wherein the materials employed consist of the hydantoin, calcium hydroxide, and water.

9. A process according to claim 3 where $R_3$ is hydrogen or one to four carbon atom alkyl or $R_2$ or $R_3$ together are an alkylene group having three to five carbon atoms.

10. The process for the preparation of the calcium salt of p-hydroxyphenylhydantoic acid which comprises the steps of (1) reacting p-hydroxyphenmylhydantoin with an aqueous solution of calcium hydroxide at from about 50° C. to about 180° C. for a sufficient period of time to form the calcium salt of said acid; (2) cooling the resultant liquid reaction mass to below 50° C. to form solid crystals of said calcium salt of said acid; (3) separating the solid crystals from the liquid reaction mass.

11. The process as set forth in claim 10 including the additional step of subjecting the solid crystals of the calcium salt of p-hydroxyphenylhydantoic acid to decarbamoylation with nitrous acid or a water soluble salt of nitrous acid under acidic conditions to produce p-hydroxyphenylglycine.

12. The process as set forth in claim 11 including the additional step of optically resolving the p-hydroxyphenylglycine to produce D-p-hydroxyphenylglycine.

13. The process as set forth in claim 12 wherein calcium oxide is used in place of calcium hydroxide.

14. The process as set forth in claim 12 wherein calcium acetate is used in place of calcium hydroxide.

* * * * *